US009028804B2

(12) United States Patent
Nguyen et al.

(10) Patent No.: US 9,028,804 B2
(45) Date of Patent: May 12, 2015

(54) WATER RESISTANT COMPOSITIONS CONTAINING A LACTONE COMPOUND AND AN AMINE COMPOUND CHOSEN FROM AMINO ALCOHOL COMPOUNDS AND ALKOXYLATED AMINE COMPOUNDS

(75) Inventors: Nghi Van Nguyen, Edison, NJ (US); Gregory Shmuylovich, Springfield, NJ (US); Catherine Chiou, Saddle Brook, NJ (US)

(73) Assignee: L'Oreal, Paris (FR)

( * ) Notice: Subject to any disclaimer, the term of this patent is extended or adjusted under 35 U.S.C. 154(b) by 323 days.

(21) Appl. No.: 13/448,437

(22) Filed: Apr. 17, 2012

(65) Prior Publication Data
US 2013/0272975 A1  Oct. 17, 2013

(51) Int. Cl.
A61K 36/00 (2006.01)
A61K 47/18 (2006.01)
A61K 8/41 (2006.01)
A61K 8/97 (2006.01)
A61Q 15/00 (2006.01)
A61K 8/45 (2006.01)
A61Q 1/02 (2006.01)
A61Q 5/06 (2006.01)
A61Q 5/12 (2006.01)
A61K 36/185 (2006.01)
A61Q 1/10 (2006.01)
A61K 8/49 (2006.01)
A61Q 5/04 (2006.01)
A61Q 17/04 (2006.01)

(52) U.S. Cl.
CPC ... *A61K 8/45* (2013.01); *A61K 8/41* (2013.01); *A61Q 1/02* (2013.01); *A61Q 5/04* (2013.01); *A61Q 5/06* (2013.01); *A61Q 5/12* (2013.01); *A61Q 15/00* (2013.01); *A61Q 17/04* (2013.01); *A61K 8/97* (2013.01); *A61K 36/185* (2013.01); *A61Q 1/10* (2013.01); *A61K 8/498* (2013.01)

(58) Field of Classification Search
CPC ........... A61K 8/41; A61K 8/42; A61K 8/498; A61K 8/92; A61K 8/97; A61K 47/10; A61K 47/14; A61K 47/06
USPC .............................. 424/59, 63, 65, 70.1, 70.2
See application file for complete search history.

(56) References Cited

U.S. PATENT DOCUMENTS

| 3,406,238 A | 10/1968 | Freyermuth et al. |
| 4,104,296 A | 8/1978 | Pike |
| 4,591,652 A | 5/1986 | DePasquale et al. |
| 5,646,321 A | 7/1997 | O'Lenick, Jr. |
| 5,741,919 A | 4/1998 | O'Lenick, Jr. |
| 5,817,846 A | 10/1998 | O'Lenick, Jr. |
| 6,022,982 A | 2/2000 | Isbell et al. |
| 6,201,144 B1 | 3/2001 | Isbell et al. |
| 6,372,203 B1 * | 4/2002 | Allwohn et al. ........... 424/70.13 |
| 6,919,076 B1 * | 7/2005 | Green et al. ................. 424/94.5 |
| 7,615,231 B2 | 11/2009 | Wohlman |
| 2002/0155962 A1 | 10/2002 | Cincotta et al. |
| 2006/0093634 A1 * | 5/2006 | Lutz et al. ..................... 424/401 |
| 2007/0092465 A1 | 4/2007 | Wohlman |
| 2009/0169502 A1 | 7/2009 | Quadir |
| 2009/0324506 A1 * | 12/2009 | Seidling et al. ................. 424/45 |
| 2010/0255046 A1 | 10/2010 | Alanzo et al. |
| 2010/0310491 A1 | 12/2010 | Falk et al. |

FOREIGN PATENT DOCUMENTS

| EP | 1283030 A1 | 2/2003 |
| JP | 62-297366 | 12/1987 |
| KR | 2010/114416 A | 10/2010 |
| WO | WO 92/06778 A1 | 4/1992 |
| WO | 97/45505 A1 | 12/1997 |
| WO | WO 99/021825 A1 | 5/1999 |
| WO | 2007/027095 A1 * | 3/2007 |
| WO | 2009061360 A1 | 5/2009 |

OTHER PUBLICATIONS

International Search Report in PCT/EP2013/057584 completed on Oct. 22, 2013 by European Patent Office, P.B. 5818 Patentlaan2, NL-2280 HV Rijswijk.
International Search Report in PCT/EP2013/057582 mailed on Nov. 29, 2013 by the European Patent Office, P.B. 5818 Patentlaan2, NL-2280 HV Rijswijk.
Amendment filed in U.S. Appl. No. 13/448,439 dated Aug. 8, 2013.
"The Rate of Ring Opening of γ- and δ- Lactones Derived from Meadowfoam Fatty Acids", Journal of the American Oil Chemist's Society—vol. 75, No. 1 (1998), pp. 63-66.
"Synthesis of Secondary Ethers Derived from Meadowfoam Oil", Journal of the American Oil Chemist's Society—vol. 75, No. 8 (1998), p. 1021-1029.
Ahn, S., Yang, N., Lee, H. Alternative Evaluation Method In Vitro for the Water Resistant Effect of Sunscreen Products, J. of Skin Research and Technology—2008, vol. 14, p. 187-191 (first published Jul. 22, 2007).
Braida, D. et al., "Ceramide: A New Approach to Hair Protection and Conditioning"—Cosmetics & Toiletries Magazine, vol. 109, Dec. 1994, p. 49-57.
Pissavini, M., Ferrero, L., Alard,V., "Determination of the in-vitro SPF"—Cosmetics & Toiletries Magazine, vol. 118, No. 10, 2003, p. 63-72.
Sayre, R.M., "Correlation of in-vivo tests, in-vitro SPF predictions: a survey of published studies"—Cosmetics & Toiletries Magazine, vol. 108, Feb. 2003, p. 111-114.

(Continued)

*Primary Examiner* — Richard Schnizer
*Assistant Examiner* — Alma Pipic
(74) *Attorney, Agent, or Firm* — Oblon, McClelland, Maier & Neustadt, L.L.P.

(57) ABSTRACT

The present invention is directed to water-resistant compositions comprising: a reaction product of at least one lactone compound and at least one amine compound chosen from amino alcohol compounds and alkoxylated amine compounds; and optionally, at least one carrier. These water-resistant compositions are capable of providing or acting as a carrier for delivering benefits to various substrates, for example, keratinous substrates such as skin and hair, while at the same time, imparting durable or long lasting hydrophobicity and/or a protective barrier onto said substrates.

12 Claims, No Drawings

(56) References Cited

OTHER PUBLICATIONS

Berislav Markovic, Donna Laura, Mark Rerek, "A Laboratory Method for Measuring the Water Resistance of Sunscreens"—Cosmetics and Toiletries Magazine, vol. 116, No. 9, Sep. 2001, p. 61-68.
Bernard, B. A. et al., "Ceramide binding to African-American hair fibre correlates with resistance to hair breakage"—International Journal of Cosmetic Science, vol. 24, 2002, p. 1-12.
Diffey, B.L., "A method for broad-spectrum classification of sunscreens"—International Journal of Cosmetic Science, vol. 16, 2006, p. 47-52.
Stokes, R. and Diffey, B.L., "In-vitro assessment of sunscreen photostability: the effect of radiation source, sunscreen application thickness and substrate"—International Journal of Cosmetic Science, vol. 21, 1999, p. 341-351.
Ferrero, L., Pissavini, M., Marguerle, S., Zastrow,L. "Sunscreens in-vitro spectroscopy: application to UVA protection assessment and correlation with in-vitro persistent pigment darkening"—International Journal of Cosmetic Science, vol. 24, 2002, p. 63-70.
Heinrich, U., Tronnier, H., Kockott, D., Kuckuk, R., Heise, H.M., "Comparison of sun protection factors determined by an in-vivo and different in-vitro methodologies: a study with 58 different commercially available sunscreen products"—International Journal of Cosmetic Science, vol. 26, 2004, p. 79-89.
Stokes, R. P., Diffey, B.L., Dawson, L.C., Barton, S.P., "A novel in-vitro technique for measuring the water resistance of sunscreens"—International Journal of Cosmetic Science, vol. 20, 1998, p. 235-240.
Gupta, V.K., Zatz, J.L., "In-vitro method for modeling water resistance of sunscreen formulations"—International Journal of Cosmetic Science, vol. 50 (2), 1999, p. 79-90.
Greiter, F., Bilek, P., Doskoczil, S., Washutti, J., Wurst, F., "Methods for water resistance testing of sun protection products"—International Journal of Cosmetic Science, vol. 1, 1979, p. 146-157.
Wendel, V., Klette, E.., Gers-Barlag, H., "A new test method to assess the UVA protection performance of sun care products"—SOFW Journal, vol. 127, 2011, p. 12-30.
Dippe, R., Klette, E., Mann, T., Wittern, K. P., Gers-Barlag, H., "Comparison of four different in-vitro test methods to assess the UVA protection performance of sunscreen products"—SOFW Journal, vol. 131,2006, p. 36-44.
William W. Christie, "Ceramides: Chemistry, Occurrence, Biology and Analysis"—The AOCS Lipid Library, 2012, http://www.lipidlibrary.co.uk/Lipids/ceramide/index.htm.
Patricia Poh Agin "Water Resistance and extended wear sunscreens"—Dermatologic Clinics, vol. 24, 2006, p. 75-79.
Zastrow, L., Ferrero, L., Herrling, T, Groth, N., "Integrated sun protection factor: a new sun protection factor based on free radicals generated by UV irradiation"—Skin Pharmacology and Physiology, vol. 17, 2004, p. 219-231.
Sayre, R.M., Agin, P., LeVee, G.J., Marlowe, E. A., "Comparison of in-vivo and in-vitro testing sunscreening formulas"—Photochemistry and Photobiology, vol. 29, 1979, p. 559-566.
Stokes, R. P., Diffey, B.L., "The water resistance of sunscreen and day care products"—British Journal of Dermatology, vol. 140, 1999, p. 259-263.
Ferrero, L., Pissavini, M., Marguerie, S., Zastrow, L., "Importance of substrate Roughness for in-vitro UV Protection Assessment"—23rd IPSCC Congress, Orlando (FL) 2004.
Colipa, "Guidelines for evaluating Sun Product Water Resistance", Dec. 2005, http://www.colipa.com.
Babor Cosmetics America, Corp, Baborganic Pure Line Reducing (glycerin) cream; retrieved from the internet on Sep. 8, 2014; http://dailymed.nlm.nih.gov/dailymed/lookup.cfm?setid=6c723805-fb8e-462c-ac49-19c18e71bd81.
Babor Cosmetics America, Corp, Babor Baborganic Calm and Relax (panhenol) cream; retrieved from the internet on Sep. 8, 2014; http://dailymed.nlm.nih.gov/dailymed/drugInfo.cfnVid=26500.
Department of Health and Human Services, Food and Drug Administration, 21 CFR Parts 310, 352, 700 and 740, RIN 0910-AA01, Sunscreen Drug Products for Over-The-Counter Human Use; Final Monograph; Federal Register, vol. 64, No. 98, May 21, 1999, Rules and Regulations, pp. 2766627693.
Response to Final Office Action dated Sep. 17, 2013 filed in U.S. Appl. No. 13/448,439 on Jan. 17, 2014.
Response to Non Final Office Action dated Aug. 8, 2013 filed in U.S. Appl. No. 13/448,440 on Dec. 9, 2013.
Response to Final Office Action dated Feb. 21, 2014 filed in U.S. Appl. No. 13/448,440 on May 21, 2014.
Response to Advisory Action dated May 30, 2014 filed in U.S. Appl. No. 13/448,440 on Jun. 23, 2014.
Response to Non Final Office Action dated Aug. 15, 2013 filed in U.S. Appl. No. 13/448,441 on Dec. 16, 2013.
Response to Final Office Action dated Apr. 4, 2014 and Advisory Action dated Jun. 16, 2014 filed in U.S. Appl. No. 13/448,441, filed Aug. 4, 2014.
Response to Non Final Office Action dated Jan. 31, 2014 filed in U.S. Appl. No. 13/845,529, filed Jun. 2, 2014.

* cited by examiner

WATER RESISTANT COMPOSITIONS CONTAINING A LACTONE COMPOUND AND AN AMINE COMPOUND CHOSEN FROM AMINO ALCOHOL COMPOUNDS AND ALKOXYLATED AMINE COMPOUNDS

FIELD OF THE INVENTION

The present invention relates to water resistant compositions and methods of using these compositions on various substrates. More particularly, the invention is directed to a composition containing the reaction product of at least one lactone compound and at least one amine compound chosen from amino alcohol compounds and alkoxylated amine compounds.

BACKGROUND OF THE INVENTION

Consumer products such as cosmetics, personal care and household products are designed to provide a wide range of desirable properties and benefits to various substrates such as keratinous substrates, hard surfaces, and other non-keratinous substrates, for example, fabrics and personal articles. Generally, these products deliver benefit agents to a substrate. These products can also be designed to protect said substrates from extreme environmental conditions or from physical contact such as rubbing or from exposure to water, humidity, moisture or other liquids.

In particular, when keratinous substrates such as skin and hair are exposed to environmental conditions, for example, high or low humidity or to ultraviolet radiation from the sun, these substrates can lose many of their desirable properties and even become damaged. The appearance and condition of skin and hair can also be affected by ultraviolet exposure and aging. For example, skin can become dry and flaky, while hair can dry out and lose its shine or color or become frizzy and less manageable under low and high humidity conditions. Under low humidity conditions, hair can dry out and dried-out hair tends to be less shiny and more brittle. Conversely, under high humidity conditions, hair tends to absorb water causing hair to lose its shape and become unmanageable and unattractive. Furthermore, hair can lose its desirable attributes due to physical stress on the hair such as brushing and application of heat.

As a result, consumers continue to seek products such as sunscreens, skin care, hair care and hair cosmetic compositions which protect and enhance the appearance of skin and hair as well as reduce the deleterious effects of adverse environmental conditions, photo-damage, and physical stress. It is thus important to ensure that the beneficial properties of such products remain on the skin and hair by making these products water resistant and/or able to provide a protective barrier or hydrophobicity to the skin and hair as well as durable or long-lasting hydrophobicity.

Water resistant products do not easily "run off" or wash off when the skin and hair are exposed to water, rain, and tears or upon sweating nor easily transfer from the skin or hair because of normal every day activity. These products also tend to have long wearing and transfer-resistant properties, that is, they adhere longer to surfaces and to keratinous substrates. Commercial products which have these properties may require high amounts of paraffin, fatty alcohols, petrolatum, Vaseline, waxes or oils, e.g., mineral oil. Other customary barrier agents are silicones and conventional film forming agents or polymers. However, such ingredients still present many disadvantages; for example, high levels of oils and hydrocarbon-based ingredients make the skin or hair greasy, waxes can give an unpleasant aesthetic look and feel, and silicones can leave residues and may give an uncomfortable feel and wear.

Thus, there still exists a need to find other materials or compositions that can provide a water-resistant and/or protective barrier to the skin and hair and which do not require the customary barrier agents.

Thus, it is an object of the present invention to provide materials and compositions which provide a water resistant protective barrier onto skin and hair, as well as impart durable or long lasting hydrophobicity and improve the water resistance of cosmetic and personal care compositions. It is also an object of the present invention to provide a water resistant composition that can function as a carrier and/or matrix for desired benefit agents used to benefit skin and hair.

BRIEF SUMMARY OF THE INVENTION

The present invention relates to a composition containing:
(a) a reaction product of:
(i) at least one lactone compound; and
(ii) at least one amine compound; and
(b) optionally, at least one carrier;
wherein (a)(ii) is chosen from amino alcohol compounds and alkoxylated amine compounds; and
wherein the composition is water resistant.

The present invention also relates to a composition containing:
(a) at least one lactone compound;
(b) at least one amine compound; and
(c) optionally, at least one carrier;
wherein (a)(ii) is chosen from amino alcohol compounds and alkoxylated amine compounds; and
wherein the composition is water resistant.

Furthermore, the present invention relates to a method of imparting water resistance onto a substrate, the method comprising applying onto the substrate, a composition containing:
(a) a reaction product of:
(i) at least one lactone compound; and
(ii) at least one amine compound; and
(b) optionally, at least one carrier;
wherein (a)(ii) is chosen from amino alcohol compounds and alkoxylated amine compounds; and
wherein the composition is water resistant.

The present invention also relates to a method of imparting water resistance onto a substrate, the method comprising applying onto the substrate, a composition containing:
(c) a reaction product of:
(i) at least one lactone compound; and
(ii) at least one amine compound; and
(b) at least one carrier;
wherein (a)(ii) is chosen from amino alcohol compounds and alkoxylated amine compounds; and
wherein the composition is water resistant.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within ±10% of the indicated number.

"Keratinous substrates" as used herein, include, but are not limited to skin, hair, lips, and eyelashes.

"Permeating through" refers to the movement of a substance, such as water, into or out of the keratinous substrate. The term may also refer to the loss of water or to the uptake/absorption of water by the keratinous substrate.

"Film former" or "film forming agent" as used herein means a polymer or resin that leaves a film on the substrate to which it is applied, for example, after a solvent accompanying the film former has evaporated, absorbed into and/or dissipated on the substrate.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

"Non-reactive solvent" as used herein, refers to a solvent comprising one or more compounds which do not have functional groups that could compete with the reaction of the at least one amine compound chosen from amino alcohol compounds and alkoxylated amine compounds with the heterocyclic ring of the lactone compound of the present invention.

The term "anhydrous" as used herein is intended to mean that the composition is either completely free of unbound water or contains substantially no unbound water, such as, for example, no more than about 1% by weight, such as no more than about 0.5% by weight, based on the weight of each composition.

As used herein, the phrase "salts and derivatives thereof" is intended to mean all salts and derivatives comprising the same functional structure as the compound they are referring to, and that have similar properties.

"Monoacid" as used herein, refers to a compound other than the lactone compound and the amine compound chosen from amino alcohol compounds and alkoxylated amine compounds of the present invention, wherein said monoacid compound has a single carboxylic group.

As used herein, the term "applying" a composition to a keratinous substrate with a composition is intended to mean contacting the keratinous substrate, for example skin or hair, with at least one of the compositions of the invention, in any manner.

As used herein, the terms "straightening" or "straighten" or "relaxing" or "relax" the hair mean to remove the curl from the hair or reduce the degree of curl of the hair. It also means changing the shape of hair or the degree of curl in the hair to make the hair more straight. It can also mean removing or reducing the frizziness of the hair.

As used herein, "cosmetically acceptable" means that the item in question is compatible with any human keratinous substrate or material, such as human hair and human skin.

As used herein, "carrier" means a carrier that is compatible with any human keratinous substrate or material, such as human hair and human skin.

As used herein, "conditioning" means imparting to a keratinous substrate such as hair or skin at least one property chosen from combability, manageability, moisture-retentivity, luster, shine, smoothness, and softness. In case of combing, the level of conditioning on the keratinous substrate such as hair is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The compositions and methods of the present invention can comprise, consist of, or consist essentially of the essential elements and limitations of the invention described herein, as well as any additional or optional ingredients, components, or limitations described herein or otherwise useful.

It was surprisingly and unexpectedly discovered that the above-disclosed compositions and reaction products are water resistant and can be employed to impart water resistance, as well as durable or long lasting hydrophobicity and/or a protective barrier onto various substrates such as keratinous substrates and non-keratinous surfaces.

The compositions and/or reaction products of the present invention can also function as carriers and/or matrices for desired benefit or additive agents by delivering cosmetic or other desirable properties to various substrates, while allowing these properties to remain longer on the substrates.

The presence of a monoacid is not required in the compositions of the present invention in order for said compositions to be water resistant and to impart properties of product durability and lasting hydrophobicity, as well as a protective barrier, onto a substrate. In addition, the compositions of the present invention do not require the use of a film former chosen from traditional film formers in order to be water-resistant.

The compositions of the present invention may consist of cosmetic compositions for application onto hair and skin and employed to form a water-resistant protective barrier on hair, for example, to help to keep moisture in the hair and allow hair to maintain its shine or to keep moisture out of the hair under high humidity conditions and improve manageability and condition of the hair.

Such cosmetic compositions can also be employed to alter or maintain the shape of hair and could be useful to style hair, straighten hair, curl hair, retain hair curl or retain the style of the hair. These compositions can also be designed to inhibit color fading in both dyed and naturally colored hair and could be useful in coloring or altering the color of hair.

The compositions of the present invention is also useful in cosmetic applications onto substrates such as skin, lips, nails and eyelashes, such as makeup, skin care and sun care products, particularly, in allowing beneficial ingredients in these products to remain longer on these substrates.

The compositions of the present invention are water-resistant such that they are not easily removed from the substrate and/or not easily transferred from the substrate over time by normal everyday activity.

Lactone Compound

The at least one lactone compound of the present invention includes, but is not limited to, cyclic ester compounds comprising a heterocyclic ring wherein the heteroatom on the heterocyclic ring is oxygen and which are represented by the general formula (I):

and wherein:

R or R', independently, is H; a hydrocarbon radical containing from 1 to 40 carbon atoms which may be saturated or unsaturated, linear or branched, substituted or unsubstituted; or a substituent other than H or said hydrocarbon radical, such as a hydroxy group, an amino group, a sulfhydryl group, an aryl group and a halogen;

X represents an integer of 1 or more, such as an integer from between 1 to 10 or such as from 1 to 8 or such as from 1 to 6;

Y is oxygen (O) or sulfur (S); and the heterocyclic ring is saturated or unsaturated.

More particularly, the lactone compounds of the present invention include, but are not limited, to those lactone compounds comprising 3- to 8-membered rings (including the oxygen on the heterocyclic ring and the carbonyl carbon).

Examples of lactone compounds are α-lactones (3-membered ring alpha-lactones), (3-lactones (4-membered ring beta-lactones), γ-lactones (5-membered ring gamma-lactones), lactones (6-membered ring delta-lactones), and ε-lactones (8-membered ring epsilon-lactones).

In preferred embodiments of the present invention, the lactone compounds of the present invention include, but are not limited to, δ-lactone (delta-lactone) compounds corresponding to the formula (II):

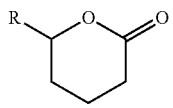
(II)

wherein R is chosen from H, a hydrocarbon radical containing from 1 to 40 carbon atoms, a hydroxyl group, an amino group, a sulfhydryl group, an aryl group, and a halogen;

wherein when R is a hydrocarbon radical, R may be linear or branched, saturated or unsaturated, substituted or unsubstituted;

wherein the carbon atoms on the lactone ring, other than the R-substituted carbon atom and the carbon on the ketone group, may be substituted; and wherein the heterocyclic ring is saturated or unsaturated.

Examples of δ-lactone compounds of the present invention are meadowfoam delta-lactone, delta-octalactone, delta-decalactone, delta-nonalactone, undecanoic delta-lactone, delta-dodecalactone, massoia lactone (or 5-pentylpent-2-en-5-olide), jasmine lactone (or Z-2-pentenylpentan-5-olide), 6-Pentyl-alpha-pyrone (or 5-Pentylpenta-2,4-dien-5-olide) delta-valerolactone, galactonolactone, glucono delta-lactone, hexadecanolactone, and mevalonolactone.

Examples of γ-lactone compounds of the present invention are gamma valerolactone, gamma hexylactone, gamma hepatalactone, gamma otalactone, gamma nonalactone, gamma decalactone, gamma undecalactone and gamma dodecalactone.

The at least one lactone compound of the present invention as based on formula (I) can be a thiocarbonyl analog of the lactone compound wherein Y in formula (I) is sulfur.

The at least one lactone compound of the present invention may also be chosen from lactone compounds wherein the heteroatom on the heterocyclic ring can be nitrogen or sulfur. When the heteroatom on the heterocyclic ring is nitrogen, the lactone compound may be chosen from lactam compounds and their thiocarbonyl analogs. When the heteroatom on the heterocyclic ring is sulfur, the lactone compound may be chosen from thiolactone compounds and their thiocarbonyl analogs.

A particularly preferred lactone compound of formula (I) for use in the present invention is the δ-lactone compound, meadowfoam delta-lactone, commercially available from The Fanning Corporation under the tradename Meadowlactone® and corresponding to formula (III):

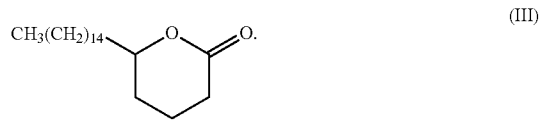
(III)

The at least one lactone compound is employed in an amount ranging from about 0.01% to about 99.99% by weight, or preferably from about 0.01% to about 70% by weight, or preferably from about 0.05% to about 50% by weight, or more preferably from about 0.1% to about 40% by weight, or even more preferably from about 0.1% to about 10% by weight, based on the total weight of the composition of the present invention, including all ranges and subranges therebetween.

Amine Compound

In accordance with the present invention, the at least one amine compound is chosen from amino alcohol compounds and alkoxylated amine compounds.

The amino alcohol compound, includes, but is not limited to amino alcohol compounds corresponding to the general formula (IA):

(IA)

wherein:

R is a H or a methyl group which is optionally substituted with a hydroxyl group or a hydrocarbon radical containing at least two carbon atoms wherein the hydrocarbon radical can be linear or branched, acyclic or cyclic, saturated or unsaturated, aliphatic or aromatic, substituted or unsubstituted, and optionally substituted with at least one hydroxyl group, and optionally interrupted with at least one radical, which may be identical or different, chosen from —C(O)NH—, —C(O)—, —OC(O)—, —C(O)O—, and —S—; and R' is a methyl group which is substituted with a hydroxyl group or a hydrocarbon radical containing at least two carbon atoms wherein the hydrocarbon radical is substituted with at least one hydroxyl group and wherein the hydrocarbon radical can be linear or branched, acyclic or cyclic, saturated or unsaturated, aliphatic or aromatic, substituted or unsubstituted and optionally interrupted with at least one radical, which may be identical or different, chosen from —C(O)NH—, —C(O)—, —OC(O)—, —C(O)O—, and —S—.

Typically, the hydrocarbon radical is a linear or branched acyclic $C_{2-22}$ alkyl or alkenyl group or a $C_{2-40}$ alkyl or alkenyl group or a $C_{2-40}$ alkyl phenyl group, more typically a $C_{6-22}$ alkyl or alkenyl group or a $C_{4-18}$ alkyl phenyl group.

The hydrocarbon radical may also be an alkyl group derived from coconut oil or from soy.

The amino alcohol compounds of the present invention may comprise, for example, a single hydroxyl group and a single amine group or alternatively, a single hydroxyl group and two or more amine groups or alternatively, two or more hydroxyl groups and a single amine group or alternatively, two or more hydroxyl groups and two or more amine groups.

Suitable amino alcohol compounds of the present invention may be selected from monoamino alcohol compounds, polyamino monoalcohol compounds, and polyamino polyalcohol compounds.

Examples of amino alcohols for use in accordance with the present invention include, but are not limited to, aminomethyl propanol, aminomethyl propanediol, aminoethyl propanediol, 2-aminobutanol, ethanolamine, and isopropanolamine.

The at least one amine compound of the present invention may also be an alkoxylated amine compound. The alkoxylation is provided by an alkylene oxide group which is preferably chosen from ethylene oxide and propylene oxide.

Non-limiting preferred examples of suitable alkoxylated amines include alkoxylated monoamine compounds corresponding to the formula (IIA):

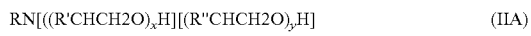
RN[((R'CHCH2O)$_x$H][(R"CHCH2O)$_y$H]  (IIA)

wherein:
R is chosen from a H, and a hydrocarbon radical containing at least 1 carbon atom and which can be linear or branched, saturated or unsaturated, aliphatic or aromatic, substituted or unsubstituted and optionally interrupted with at least one radical, which may be identical or different, chosen from —C(O)NH—, —C(O)—, —OC(O)—, —C(O)O— and —S—;
x and y, independently of one another, represent numbers of from 0 to 100 provided that the sum of x+y is >0;
the groups R' and R", which may be identical or different, represent hydrogen, or an alkyl group such as a methyl group; such that x or y is 0 when R is a hydrocarbon radical containing at least 1 carbon atom and which can be linear or branched, saturated or unsaturated, aliphatic or aromatic, substituted or unsubstituted and optionally interrupted with at least one radical, which may be identical or different, chosen from —C(O)NH—, —C(O)—, —OC(O)—, —C(O)O—, and —S—.

Typically, x and y, independently of one another, are each a number from 0 to 30.

Other non-limiting examples of suitable alkoxylated monoamine compounds include those corresponding to formula (IIIA):

RNR"[(R'CHCH2O)$_x$H]  (IIIA)

wherein:
R is chosen from a H, and a hydrocarbon radical containing at least 6 carbon atoms and which can be linear or branched, saturated or unsaturated, aliphatic or aromatic, substituted or unsubstituted and optionally interrupted with at least one radical, which may be identical or different, chosen from —C(O)NH—, —C(O)—, —OC(O)—, —C(O)O—, and —S—;
x represents a number of from 1 to 100;
R' represents hydrogen, or an alkyl group such as in particular a methyl group; and
R" is a hydrogen or a hydrocarbon radical containing at least 6 carbon atoms and which can be linear or branched, saturated or unsaturated, aliphatic or aromatic, substituted or unsubstituted and optionally interrupted with at least one radical, which may be identical or different, chosen from —C(O)NH—, —C(O)—, —OC(O)—, —C(O)O—, and —S—;

Typically, x is a number from 1 to 30.

When R" in formula (IIIA) is a hydrocarbon radical group, it may also contain an alkoxylated moiety (as defined by [(R'CHCH$_2$O)$_y$H]), and/or heteroatoms such as nitrogen.

When R" contains at least one alkoxylated moiety, the total number of alkoxylation in the formula may range from 1 to 120.

Additional non-limiting examples of alkoxylated monoamine compounds include those corresponding to formula (IVA):

R(R'CHCH2O)$_x$(R'CHCH2O)$_y$NH2  (IVA)

wherein:
R is a hydrocarbon radical containing at least 1 carbon atom; R can be linear or branched, saturated or unsaturated, aliphatic or aromatic, substituted or unsubstituted and optionally interrupted with at least one radical, which may be identical or different, chosen from —C(O)NH—, —C(O)—, —OC(O)—, —C(O)O—, and —S—;
x and y, independently of one another, represent numbers of from 0 to 100 with the proviso that the sum of x+y is >0;
the groups R', which may be identical or different, represent hydrogen, or an alkyl group such as in particular a methyl group.

Typically, R is a linear or branched, acyclic alkyl or alkenyl group or an alkyl phenyl group; x and y, independently of one another, are each typically a number from 0 to 30.

Examples of alkoxylated monoamines for use in the present invention which correspond to formula (VII) are polyetheramines containing a monoamine group. These polyetheramines are commercially available from Hunstman under the tradename Jeffamine (M series such as M-600, M-1000, M-2005 and M-2070) and Surfonamine series (B-60, B-100, B-200, L-100, L-200, L-207, L-300).

The alkoxylated monoamines for use in the present invention may also be chosen from aminosilicones having one amino group and at least one degree of alkoxylation.

The alkoxylated amine compounds of the present invention may also be chosen from alkoxylated polyamine compounds having at least two amino groups and at least one degree of alkoxylation. The alkoxylation is provided by an alkylene oxide group which is preferably chosen from ethylene oxide and propylene oxide.

Non-limiting preferred examples of suitable alkoxylated polyamine compounds include those corresponding to formula (VA):

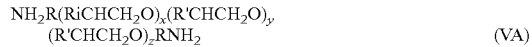
NH$_2$R(RiCHCH$_2$O)$_x$(R'CHCH$_2$O)$_y$(R'CHCH$_2$O)$_z$RNH$_2$  (VA)

wherein:
R represents a —CH2—, —CH$_2$CH$_2$—, —CHCH$_3$— or —C(CH$_3$)$_2$— group, or a hydrocarbon radical containing at least 3 carbon atoms that is linear or branched, saturated or unsaturated, aliphatic or aromatic, substituted or unsubstituted and optionally interrupted with at least one radical, which may be identical or different, chosen from —C(O)NH—, —C(O)—, —OC(O)—, —C(O)O—, and —S—; x, y, and z independently of one another, represent numbers of from 0 to about 100;
R' represents hydrogen, or an alkyl group, preferably a methyl group; and the sum of x+y+z is at least 1.

In formula (VA), R is preferably a linear or branched, acyclic alkyl or alkenyl group or an alkyl phenyl group; x, y, and z independently of one another, preferably represent numbers ranging from 2 to 100.

Examples of the alkoxylated polyamines for use in the present invention which correspond to formula (VA) include, for example, tetradecyloxypropyl-1,3-diaminopropane; a C12-14 alkyl oxypropyl-1,3-diaminopropane; a C12-15 alkyloxypropyl amine and other similar materials that are commercially available from Tomah under the tradename of TOMAH® DA-17.

Other examples of alkoxylated polyamines of Formula (VA) are diamine compounds belonging to the Jeffamine series such as the Jeffamine® D and Jeffamine® ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. Jeffamine® D series compounds are amine terminated PPGs (polypropylene glycols) and Jeffamine® ED series compounds are polyether diamine based with a predominantly PEG (polyethylene glycol) backbone.

Other non-limiting preferred examples of suitable alkoxylated polyamine compounds in the diamine form include those corresponding to formula (VIA):

$$NH_2(CH_2)_xOCH_2CH_2O(CH_2)_xNH_2 \quad (VIA)$$

wherein x is 2 or 3.

Examples of alkoxylated polyamines of Formula (VIA) are diamine compounds belonging to the JEFFAMINE series available from Huntsman Corporation, Salt Lake City, Utah, such as JEFFAMINE EDR148, and JEFFAMINE EDR176.

Additional non-limiting preferred examples of alkoxylated polyamines in the triamine form include compounds corresponding to formula (VIIA):

$$NH_2(CHCH_3CH_2O)_xCH_2C(R)CH_2(OCH_2CHCH_3)_zNH_2 \\ | \\ (CH_2)_n(OCH_2CHCH_3)_yNH_2 \quad (VIIA)$$

wherein:

R is hydrogen, —$CH_2$ or —$C_2H_5$, n=0 or 1, and x, y, and z independently of one another, represent numbers of from 0 to 100 and the sum of x+y+z is at least 1.

Examples of alkoxylated polyamine compounds for use in the present invention which correspond to formula (VIIA) are triamine compounds belonging to the Jeffamine series such as the Jeffamine® T series available from Huntsman Corporation, Salt Lake City, Utah. Examples of the Jeffamine® T series compounds are JEFFAMINE T403, JEFFAMINE T3000, and JEFFAMINE T5000. Jeffamine® T series compounds are triamines made by reacting PO with a triol initiator followed by aminating the terminal hydroxyl groups.

Another type of preferred alkoxylated polyamines include compounds of formulas (VIIIA) and (IXA) hereunder:

$$RNH{-}\left[\begin{array}{l} C_3H_5OH \\ | \\ O(CH_2CH_2O)_nC_3H_5OH \\ | \\ NH(CH_2)_mNH \\ \quad | \qquad\quad | \\ \quad C_3H_5OH \quad OH \\ \quad | \qquad\quad | \\ \quad O(CH_2CH_2OC_3H_5 \\ \qquad\qquad\quad | \\ \qquad\qquad\quad NHR \end{array}\right]_x \quad (VIIIA)$$

$$RNH{-}\left[\begin{array}{l} C_3H_5OH \\ | \\ O(CH_2CH_2O)_nC_3H_5OH \\ | \\ NH(CH_2)_mNH \\ | \\ C_3H_5OH \\ | \\ O(CH_2CH_2O)_n \\ | \\ C_3H_5OH \\ | \\ RNH \end{array}\right]_x \quad (IXA)$$

wherein:

R in formula (VIIIA) represents the alkyl group derived from tallow and R in formula (IXA) represents the alkyl group derived from coconut oil;

n in both formulas (VIIIA) and (IXA) has a total value ranging from 10 to 20;

m in both formulas (VIIIA) and (IXA) has a value ranging from 2 to 6; and x in both formulas (VIIIA) and (IXA) has a value ranging from 2 to 4.

Other preferred types of alkoxylated polyamines include aminosilicones with at least one degree of alkoxylation.

Preferred examples of alkoxylated polyamines for use in the present invention include compounds of Formulas (VIIIA) and (IXA) above. such as PEG-15 Tallow Polyamine and PEG-15 Cocopolyamine, respectively Particularly preferred amino alcohol compounds of the present invention are chosen from aminomethyl propanol, also known by the tradenames, AMP ULTRA PC 3000 and AMP ULTRA PC 2000, and aminomethyl propanediol, also known by tradename, AMPD ULTRA PC, all commercially available from The Dow Chemical Company.

The at least one amine compound of the present invention is employed in an amount ranging from about 0.01% to about 99.99% by weight, or preferably from about 0.01% to about 70% by weight, or preferably from about 0.05% to about 50% by weight, or more preferably from about 0.1% to about 40% by weight, or even more preferably from about 0.1% to about 10% by weight, based on the total weight of the composition of the present invention, including all ranges and subranges therebetween.

The at least one lactone compound and the at least one amine compound may be present in the compositions of the present invention in a combined amount of from about 0.01% to about 50% by weight, such as from about 0.05% to about 40% by weight, such as from about 0.1% to about 30% by weight, such as from about 0.25% to about 20% by weight, or such as from about 0.5% to about 10% by weight, based on the total weight of the compositions of the present invention, including all ranges and subranges therebetween.

Reaction Product

The combination of the at least one lactone compound with the at least one amine compound of the present invention may result in the formation of a reaction product.

Although not wanting to be bound by any particular theory, it is believed that the amine group(s) of the at least one amine compound of the present invention reacts with the carbonyl group or thiocarbonyl group on the heterocyclic ring of the at least one lactone compound of the present invention, resulting in the opening of the heterocyclic ring and in the formation of the reaction product of the present invention. The reaction product may comprise at least one amide linkage and at least one ester linkage.

It is not necessary for all amine or hydroxyl groups and all carbonyl groups or thiocarbonyl groups to react with each other to form the reaction products. Rather, it is possible that the compositions of the present invention may contain free amine compound and/or free lactone compound in addition to the reaction products.

The appropriate amount of the lactone compound to react with the amine compound to obtain the reaction products of the present invention can be easily determined.

In preferred embodiments of the present invention, the molar ratio of the at least one lactone compound to the at least amine compound ranges from between about 10:1 to about 1:10, such as from about 8:1 to about 1:8, such as from between about 5:1 to about 1:5, such as from between about 3:1 to about 1:3, such as from between about 2:1 to about 1:2, including all ranges and subranges therebetween.

In particularly preferred embodiments, the molar ratio of the at least one lactone compound to the at least one amine compound is about 1:1 or about 1:2 or about 2:1.

According to preferred embodiments of the present invention, when at least one of the carbon atoms on the heterocyclic ring of the at least one lactone compound is substituted with a hydrocarbon radical containing at least 6 carbon atoms, the at least one amine compound does not require a substituent comprising at least one hydrocarbon radical containing at least 6 carbon atoms.

According to other preferred embodiments of the present invention, when none of the carbon atoms on the heterocyclic ring of the at least one lactone compound is substituted with a hydrocarbon radical containing at least 6 carbon atoms, the at least one amine compound contains a substituent comprising at least one hydrocarbon radical containing at least 6 carbon atoms.

In preferred embodiments of the present invention, the reaction product has at least one substitutent comprising a hydrocarbon radical containing at least 6 carbon atoms. According to particularly preferred embodiments, the reaction product of the present invention is of the monoamide type or monoester type.

In other preferred embodiments, the reaction product of the present invention is of the polyamide type or polyester type.

Without being bound to any particular theory, it is also believed that other functional groups on the reaction product of the lactone compound and the amine compound may further react or interact with the carbonyl group or thiocarbonyl group of any unreacted lactone compound.

According to preferred embodiments, the lactone compound and the amine compound are mixed together at room temperature under anhydrous conditions. The mixture is then preferably heated beyond the melting point of the amine and/or of the lactone compound, or of the mixture of the amine compound and the lactone compound, typically up to about 100° C. or 110° C. or 120° C. for at least about 30 minutes, or for at least about 60 minutes, or for at least about 120 minutes, including all time intervals therein, to form the reaction product of the present invention.

In some embodiments, the reaction product of the lactone compound and the amine compound may be employed as a cosmetic, personal care or dermatological composition.

In other embodiments, any unreacted or excess lactone compound or amine compound may constitute a carrier such that the resulting reaction product may be employed as a cosmetic, personal care or dermatological composition.

The reaction product of the present invention may be in the form of a solid or in the form of a liquid.

In preferred embodiments, the reaction product of the present invention is combined with at least one carrier to form a composition such as a cosmetic, personal care or dermatological composition.

In other preferred embodiments, the reaction product of the present invention of the present invention is combined with compositions comprising at least one benefit agent.

In other preferred embodiments, the lactone compound and the amine compound are mixed together at room temperature under anhydrous conditions in the presence of at least one anhydrous, non-reactive solvent. The reaction product may be formed at room temperature or the lactone compound-amine compound mixture may heated beyond the melting point of the amine and/or of the lactone compound, or of the mixture of the amine compound and the lactone compound, typically up to about 100° C. or 110° C. or 120° C. for at least about 30 minutes, or for at least about 60 minutes, or for at least about 120 minutes, including all time intervals therein, to form the reaction product of the present invention.

The anhydrous, non-reactive solvent in which the reaction product can be prepared may be chosen from oils, organic solvents, esters, and silicones and may include, but is not limited to, hydrocarbon-based compounds such as isododecane, isohexadecane, paraffin, isoparaffin, and mineral oil, and silicone oils such as dimethicone.

In some embodiments, the reaction product that is prepared in at least one anhydrous, non-reactive solvent may be in a ready-to-use form and may be used as a cosmetic, personal care or dermatological composition.

In other embodiments, the reaction product that is prepared in at least one anhydrous, non-reactive solvent is combined with at least one carrier or with compositions comprising at least one benefit agent.

It was surprisingly and unexpectedly discovered that the compositions containing the reaction product of the present invention are water resistant and provide water resistant properties and long lasting and durable hydrophobicity to the surface of keratinous substrates. Moreover, said compositions are stable and are capable of carrying various types of ingredients, such as benefit agents.

It was also surprisingly and unexpectedly discovered that the compositions containing the reaction product of the present invention have improved water resistance properties when applied onto keratinous substrates.

The amount of the reaction product ranges from about 0.01% to about 50% by weight, such as from about 0.05% to about 40% by weight, such as from about 0.1% to about 30% by weight, such as from about 0.25% to about 20% by weight, or such as from about 0.5% to about 10% by weight, based on the total weight of the compositions of the present invention, including all ranges and subranges therebetween.

The presence of a monoacid is not required in the compositions or in forming the reaction product of the present invention, in order for said compositions and reaction product to be water resistant.

Carrier

The at least one carrier of the present invention may be an anhydrous carrier or an emulsion carrier or an aqueous carrier or aqueous-alcoholic carrier or an alcoholic carrier or a solid carrier or a vaporizable carrier. When it is an emulsion, it may be an oil-in-water emulsion, water-in-oil emulsion, silicone-in-water emulsion, or water-in-silicone emulsion.

In preferred embodiments of the present invention, the at least one carrier comprises water, oils, alcohols, organic solvents, esters, silicones, waxes, and mixtures thereof.

In other preferred embodiments, the at least one carrier comprises and/or includes either the at least one lactone compound or the at least one amine compound, whichever one is in excess and remains unreacted after the reaction product of the present invention is formed.

Suitable oils that may comprise the carrier include, but are not limited to, mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate sold under the trade name Finsolv® TN, commercially available from Innospec or Tegosoft® TN, commercially available from Evonik Goldschmidt, octyl palmitate, isopropyl lanolate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Other oils that may comprise the carrier may include for example: silicone oils, for instance volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyl-trisiloxanes or 2-phenylethyl trimethylsiloxy silicates, and polymethylphenylsiloxanes; mixtures thereof. Particularly representative of such oils are volatile silicone oils, such as cyclomethicones.

Other suitable oils include, but are not limited to, volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar™ or Permethyl®, and their mixtures.

Examples of other oils also include branched and unbranched hydrocarbons and hydrocarbon waxes including polyolefins, in particular petrolatum, paraffin oil, squalane, squalene, hydrogenated polyisobutene, hydrogenated polydecene, polybutene, pentahydrosqualene, and mixtures thereof Among the alcohols and organic solvents that may be mentioned are lower alcohols such as ethanol, fatty alcohols and polyols. The fatty alcohols may be chosen from those of the formula R—OH where R represents a linear or branched higher fatty acid residue containing from 8 to 40 carbon atoms. The polyols may be chosen from glycols and glycol ethers, for instance glycerol, ethylene glycol, propylene glycol, butylene glycol, dipropylene glycol or diethylene glycol.

Suitable esters that may comprise the carrier include, but are not limited to, esters of formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate, and pentaerythritol esters.

Other suitable esters that may comprise the carrier include polyesters, alkoxylated esters, and alkoxylated polyesters.

Suitable silicones that may comprise the carrier include, but are not limited to, the silicone oils described above and other silicones such as non-volatile silicones such as dimethicone fluids having viscosity values of equal to or greater than 300 cst, and pentaphenyldimethicone, also known as trimethyl pentaphenyl trisiloxane, commercially available from Dow Corning under the tradename Dow Corning® 555.

Suitable waxes that may comprise the carrier include, but are not limited to, those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil; synthetic waxes such as the polyethylene waxes obtained from the polymerization or copolymerization of ethylene, and Fischer-Tropsch® waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST® 2T-4S, and mixtures thereof.

The at least one carrier of the present invention may comprise a non-reactive solvent.

In preferred embodiments, the at least one carrier of the present invention may comprise a cosmetically or physiologically acceptable medium that is non toxic, wherein the compositions can be applied onto keratinous substrates such the skin, lips, hair, scalp, lashes, brows, nails or any other cutaneous region of the body. The cosmetically or physiologically acceptable medium may comprise one or more of the oils, solvents and carriers mentioned above.

In preferred embodiments of the present invention, the cosmetically or physiologically acceptable medium comprises water, oils, alcohols, organic solvents, esters, silicones, waxes, and mixtures thereof.

The carrier can be employed in an amount of from about 0.01% to about 99.98% by weight, such as from about 1% to about 99% by weight, or such as from about 2% to about 90% by weight, or such as from about 5% to about 80% by weight, and from about 10% to about 70% by weight, based on the total weight of the composition.

Benefit Agent

The compositions of the present invention may further comprise at least one benefit agent which includes, but is not limited to, sunscreen agents, cosmetically and dermatologically active agents, humectants and moisturizing agents, colorants, hair straightening/relaxing agents, film forming agents, shine agents, conditioning agents, reducing agents, emollients, vitamins, antidandruff agents, plant extracts, antiperspirants, and pharmaceutical agents.

Representative sunscreen agents may be chosen from organic and inorganic sunscreens or UV filters.

The organic sunscreen agents are selected from water-soluble organic screening agents, fat-soluble organic screening agents or agents which are insoluble in the solvents presently included in suntan products, and mixtures thereof.

The organic sunscreen agents are especially selected from cinnamic derivatives; anthranilates; salicylic derivatives; dibenzoylmethane derivatives; camphor derivatives; benzophenone derivatives; beta, beta-diphenylacrylate derivatives; triazine derivatives; benzotriazole derivatives; benzalmalonate derivatives; benzimidazole derivatives;

imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; alpha-alkylstyrene-derived dimers; 4,4-diarylbutadienes; merocyanin derivatives; and mixtures thereof.

Examples of complementary organic photoprotective agents include those denoted hereinbelow under their INCI name:

Cinnamic Derivatives:

Ethylhexyl Methoxycinnamate marketed in particular under the trademark "Parsol MCX®" by DSM Nutritional Products, Inc., Isopropyl Methoxycinnamate, Isoamyl p-Methoxycinnamate marketed under the trademark "Neo Heliopan E 1000©" by Symrise, DEA Methoxycinnamate, Diisopropyl Methylcinnamate, Glyceryl Ethylhexanoate Dimethoxycinnamate.

Dibenzoylmethane Derivatives: [Butyl Methoxydibenzoylmethane marketed especially under the trademark "Parsol 1789®" by DSM Nutritional Products, Inc., Isopropyl Dibenzoylmethane.

Para-Aminobenzoic Acid Derivatives: PABA, Ethyl PABA, Ethyl Dihydroxypropyl PABA, Ethylhexyl Dimethyl PABA marketed in particular under the trademark "Escalol 507®" by ISP, Glyceryl PABA, PEG-25 PABA marketed under the trademark "Uvinul P25®" by BASF.

Salicylic Derivatives: Homosalate marketed under the trademark "Eusolex HMS®" by Merck KGaA/EMD Chemicals, Inc. and EMD Chemicals Inc, Ethylhexyl Salicylate marketed under the trademark "Neo Heliopan OS®" by Symrise, Dipropylene Glycol Salicylate marketed under the trademark "Dipsal™" by Lubrizol Advanced Materials, Inc., TEA Salicylate marketed under the trademark "Neo Heliopan® TS" by Symrise. beta, beta-Diphenylacrylate Derivatives:

Octocrylene marketed in particular under the trademark "Uvinul N539T®" by BASF, Etocrylene marketed in particular under the trademark "Uvinul® N35" by BASF.

Benzophenone Derivatives: Benzophenone-1 marketed under the trademark "Uvinul® 400" by BASF, Benzophenone-2 marketed under the trademark "Uvinul® D50" by BASF, Benzophenone-3 or Oxybenzone marketed under the trademark "Uvinul® M40" by BASF, Benzophenone-4 marketed under the trademark "Uvinul® MS40" by BASF, Benzophenone-5, Benzophenone-6 marketed under the trademark "Helisorb® 11" by Norquay, Benzophenone-8, Benzophenone-9, Benzophenone-12, n-Hexyl 2-(4-diethylamino-2-hydroxybenzoyl)benzoate marketed under the trademark "Uvinul® A+" by BASF.

Benzylidenecamphor Derivatives: 3-Benzylidenecamphor manufactured under the trademark "Mexoryl™ SD" by Chimex, 4-Methylbenzylidenecamphor marketed under the trademark "Eusolex® 6300" by Merck, Benzylidene Camphor Sulfonic acid manufactured under the trademark "Mexoryl™ SL" by Chimex, Camphor Benzalkonium Methosulfate manufactured under the trademark "Mexoryl™ SO" by Chimex, Terephthalylidene Dicamphor Sulfonic acid manufactured under the trademark "Mexoryl™ SX" by Chimex, Polyacrylamidomethyl Benzylidene Camphor manufactured under the trademark "Mexoryl™ SW" by Chimex.

Phenylbenzimidazole Derivatives: Phenylbenzimidazole Sulfonic acid marketed in particular under the trademark "Eusolex® 232" by Merck and EMD INC., Disodium Phenyl Dibenzimidazole Tetrasulfonate marketed under the trademark "Neo Heliopan® AP" by Symrise.

Phenylbenzotriazole Derivatives: Drometrizole Trisiloxane, Methylene bis(Benzotriazolyl) Tetramethylbutylphenol, or in micronized form as an aqueous dispersion under the trademark "Tinosorb® M" by BASF.

Triazine Derivatives: bis-Ethylhexyloxyphenol Methoxyphenyl Triazine marketed under the trademark "Tinosorb® S" by BASF, Ethylhexyl Triazone marketed in particular under the trademark "Uvinul® T150" by BASF, Diethylhexyl Butamido Triazone marketed under the trademark "Uvasorb® HEB" by 3V Group, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltrisiloxane)-s-triazine, 2,4-Bis(dineopentyl 4'-aminobenzalmalonate)-6-(n-butyl 4'-aminobenzoate)-s-triazine, triazine agents, especially 2,4, 6-tris(biphenyl-1,3,5-triazines (in particular 2,4,6-tris(biphenyl-4-yl)-1,3,5-triazine and 2,4,6-tris(terphenyl)-1,3,5-triazine.

Anthranilic Derivatives: Menthyl anthranilate marketed under the trademark "Neo Heliopan® MA" by Symrise.

Imidazoline Derivatives: Ethylhexyl Dimethoxybenzylidene Dioxoimidazoline Propionate.

Benzalmalonate Derivatives: Polyorganosiloxane containing benzalmalonate functions, for instance Polysilicone-15, marketed under the trademark "Parsol® SLX" by DSM Nutritional Products, Inc.

4,4-Diarylbutadiene Derivatives: 1,1-Dicarboxy(2,2'-dimethylpropyl)-4,4-diphenylbutadiene.

Benzoxazole derivatives: 2,4-Bis[5-(1-dimethylpropyl)benzoxazol-2-yl(4-phenyl)imino]-6-(2-et-hylhexyl)imino-1, 3,5-triazine marketed under the trademark Uvasorb K 2A by Sigma 3V, and mixtures thereof.

The preferred organic sunscreen agents are selected from: Ethylhexyl Methoxycinnamate, Ethylhexyl Salicylate, Homosalate, Butyl Methoxydibenzoylmethane, Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene camphor, Terephthalylidene Dicamphor Sulfonic Acid, Disodium Phenyl Dibenzimidazole Tetrasulfonate, Methylene bis-Benzotriazolyl Tetramethylbutylphenol, Bis-Ethylhexyloxyphenol Methoxyphenyl Triazine, Ethylhexyl Triazone, Diethylhexyl Butamido Triazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltrisiloxane)-s-triazine, 2,4-Bis (dineopentyl 4'-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15,1,1-Dicarboxy(2,2'-dimethylpropyl)-4,4-diphenylbutadiene, 2,4-Bis[5-1-(dimethylpropyl)benzoxazol-2-yl(4-phenyl)imino]-6-(2-et-hylhexyl)-imino-1,3,5-triazine, and mixtures thereof.

Examples of inorganic sunscreen agents or UV filters include, but are not limited to, metal oxide pigments which may be chosen from zinc oxide, titanium oxide, iron oxide, zirconium oxide, cerium oxide, and mixtures thereof.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

The sunscreen agents of the present invention may be employed in an amount of from about 0.1% to about 40% by weight, such as from about 0.5% to about 30% by weight, such as from about 1% to about 25% by weight, based on the total weight of the composition.

Representative cosmetically and dermatologically active agents include, but are not limited to:
 antipollution agents and/or free-radical scavengers;
 depigmenting agents and/or propigmenting agents;
 self-tanning agents;
 anti-acne agents;
 anti-aging agents;
 antiglycation agents;
 NO-synthase inhibitors;
 agents for stimulating the synthesis of dermal or epidermal macromolecules and/or for preventing their degradation;
 agents for stimulating fibroblast proliferation;
 agents for stimulating keratinocyte proliferation;
 muscle relaxants;
 tensioning agents;
 desquamating and exfoliating agents;
 moisturizers and humectants;
 anti-inflammatory agents;
 agents acting on the energy metabolism of cells;
 insect repellants;
 substance P or CGRP antagonists.

Suitable examples of humectants and moisturizing agents include, but are not limited to urea, hydroxyethyl urea, polyols such as glycerin, and glycosaminoglycans (GAGs). Suitable examples of glycosaminoglycans are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS).

Acceptable colorants include, but are not limited to pigments, dyes, such as liposoluble dyes, nacreous pigments, pearling agents, direct dyes and oxidation dyes.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium.

The direct dyes and oxidation dyes which may be used in the present invention are those dyes employed to color hair. Representative oxidation dyes include, but are not limited to para-phenylenediamines, bis(phenyl)alkylenediamines, para-aminophenols, ortho-aminophenols and heterocyclic bases, and the addition salts thereof. Representative direct dyes include, but are not limited to, azo, methane, carbonyl, azine, nitro (hetero)aryl, tri(hetero)arylmethane, porphyrin, phthalocyanin direct dyes, and natural direct dyes.

The hair straightening/relaxing agents and reducing agents which may be used in the present invention are those compounds which are employed to permanently or temporarily change the shape of the hair such as, for example, hydroxide and non-hydroxide bases, amine-based compounds, and thiol-based agents.

The composition(s) of the present invention may also comprise additives, for instance those chosen from the non-exhaustive list such as rheology-modifying agents, film-forming agents, surfactants, sequestering agents, softeners, antifoams, basifying agents, gelling agents, wetting agents, thickening agents, spreading agents, dispersants, plasticizers, preservatives, pigments, mineral fillers, clays, colloidal minerals, nacres, nacreous agents, fragrances, peptizers, preserving agents, pH adjusters, fixing or non-fixing polymers, silicones, mineral, organic or plant oils, plant extracts, oxyethylenated or non-oxyethylenated waxes, paraffins, fatty acids, and the like.

According to some embodiments of the present invention, the compositions of the present invention are anhydrous.

In the event that the composition of the present invention includes water, the composition may comprise water in an amount of from about 1% to about 90% water, more preferably from about 5% to about 75% water, and more preferably from about 15% to about 50% water by weight with respect to the total weight of the composition, including all ranges and subranges therebetween.

The compositions of the present invention may be in the form of a simple or complex emulsion (oil-in-water (o/w), water-in-oil (w/o), silicone-in-water and/or water-in-silicone emulsion types) such as a cream or a milk, in the form of a gel or a cream-gel, or in the form of a lotion, a powder or a solid tube, and may optionally be packaged as an aerosol and may be in the form of a mousse or a spray. The mousse or spray may contain propellants such as for example, the hydrofluorinated compounds dichlorodifluoromethane, difluoroethane, dimethyl ether, isobutane, n-butane, propane or trichlorofluoromethane.

The emulsions of the present invention will generally contain at least one emulsifier chosen from amphoteric, anionic, cationic and nonionic emulsifiers, which are used alone or as a mixture. The emulsifiers are appropriately chosen according to the emulsion to be obtained.

As emulsifiers that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the tradename Dow Corning® DC 5225 C by the company Dow Corning, and alkyldimethicone copolyols such as laurylmethicone copolyol sold under the tradename Dow Corning® 5200 Formulation Aid by the company Dow Corning; cetyldimethicone copolyol, such as the product sold under the name Abil® EM 90R by the company Goldschmidt, and the mixture of cetyldimethicone copolyol, of polyglyceryl isostearate (4 mol) and of hexyl laurate, sold under the name Abil® WE O9 by the company Goldschmidt. One or more co-emulsifiers may also be added thereto, which may be chosen advantageously from the group comprising polyol alkyl esters. Polyol alkyl esters that may especially be mentioned include glycerol and/or sorbitan esters, for example polyglyceryl isostearate, such as the product sold under the name Isolan® GI 34 by the company Goldschmidt, sorbitan isostearate, such as the product sold under the name Arlacel 987 by the company ICI, sorbitan glyceryl isostearate, such as the product sold under the name Arlacel™ 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside sold, for example, by the company Henkel under the respective names Plantaren® 2000 and Plantaren® 1200, cetostearyl glucoside optionally as a mixture with cetostearyl alcohol, sold, for example, under the name Montanov™ 68 by the company SEPPIC, under the name Tego® Care CG90 by the company Goldschmidt and under the name Emulgade® KE3302 by the company Henkel, and also arachidyl glucoside, for example in the form of a mixture of arachidyl alcohol, behenyl alcohol and arachidyl glucoside, sold under the name Montanov® 202 by the company SEPPIC. According to one particular embodiment of the invention, the mixture of the alkylpolyglucoside as defined above with the corresponding fatty alcohol may be in the form of a self-emulsifying composition as described, for example, in document WO-A-92/06778.

In another embodiment of the invention, the subject compositions are formulated as water-in-silicone (W/Si) or silicone-in-water (Si/W) emulsions in which the continuous oily phase comprises at least one silicone oil. When the compositions of the invention are formulated as water-in-silicone emulsions, the silicone oils are preferably present in a proportion of at least 5 percent and preferably ranging from 10 percent to 45 percent by weight with respect to the total weight of the emulsion. The fatty phase of the water-in-oil emulsions according to the invention can additionally comprise one or more hydrocarbon-comprising oil(s) in a proportion preferably ranging up to 40 percent by weight with respect to the total weight of the fatty phase of the emulsion.

For the W/Si emulsions, examples of emulsifiers generally include polyether-modified silicones having a long chain of dimethyl siloxane units which carry polyethoxy-polypropoxy units in the chain and at the ends. Examples include cyclopentasiloxane PEG/PPG-18/18 dimethicone, PEG-12 Dimethicone, and PEG/PPG-19/19 Dimethicone sold by Dow Corning under the name Dow Corning® BY 11-030.

In accordance with preferred embodiments, the water resistant compositions of the present invention comprising: a reaction product of at least one lactone compound and at least one amine compound; and optionally, at least one carrier, are applied topically onto the desired area of a keratinous substrate in an amount sufficient to impart water resistance or hydrophobicity to the substrates.

In accordance with embodiments of the present invention, the water resistant compositions of the present invention comprising at least one lactone compound, at least one amine compound, and optionally, at least one carrier are applied topically to the desired area of the keratinous substrate in an amount sufficient to impart water resistance or hydrophobicity to the substrates.

In other embodiments of the present invention, the water resistant compositions of the present invention require at least one carrier.

In preferred embodiments, the disclosed compositions and reaction products of the present invention are applied onto substrates chosen from keratinous substrates such as skin and hair. In particular, the reaction product is combined with a benefit agent or with compositions containing benefit agents to improve the water resistance properties of compositions capable of providing at least one beneficial property to skin and hair, while at the same time, imparting durable or long lasting hydrophobicity as well as a protective barrier to skin and hair.

In one particularly preferred embodiment, a method of making a water resistant composition is provided wherein at least one lactone compound is combined with at least one amine compound.

In certain embodiments, a method of providing a protective barrier onto a substrate is provided, wherein said method involves applying onto the keratinous substrate, a composition containing the above-described reaction product, and optionally, at least one carrier.

In one preferred embodiment of the present invention, there is provided, a composition for and a method of preventing or reducing ultraviolet light damage to a keratinous substrate, the method comprising applying onto the keratinous substrate, a composition containing the above-described reaction product; at least one sunscreen agent; and optionally, at least one carrier.

In other preferred embodiments of the present invention, there is provided, a method of imparting water resistance onto a substrate, involving applying onto the substrate, the compositions of the present invention.

The compositions of the present invention may especially constitute cosmetic, personal care or dermatological compositions such as hair cosmetic compositions, hair care compositions, sunscreen compositions, makeup compositions, and skin care compositions.

In one embodiment, the composition of the present invention can be a hair cosmetic product such as a hair styling composition comprising the at least one lactone compound, the at least one amine compound, a hair styling agent such as film formers and waxes, and a carrier.

In another embodiment, the composition of the present invention can be a hair cleansing composition comprising the at least one lactone compound, the at least one amine compound, at least one surfactant chosen from anionic, nonionic, amphoteric/zwitterionic and cationic surfactants, and a carrier.

In yet another embodiment, the composition of the present invention can be a hair or a skin conditioning composition comprising the at least one lactone compound, the at least one amine compound, a conditioning agent such as moisturizing agents, plant extracts, cationic and quaternary compounds, and a carrier.

In other embodiments, the composition of the present invention can be a makeup product comprising the at least one lactone compound, the at least one amine compound, a first benefit agent comprising at least one colorant, optionally, a second benefit agent such as conditioning agents, moisturizing agents, emollients, sunscreen agents, and film forming agents, and a carrier.

In yet other embodiments, the composition of the present invention can be a skin care product comprising the at least one lactone compound, the at least one amine compound, a benefit agent such as sunscreen agents, cosmetically active agents, dermatologically active agents, humectants, moisturizing agents, film forming agents, conditioning agents, emollients, vitamins, plant extracts, and pharmaceutical agents, and a carrier.

The composition of the present invention may also be used as a post treatment composition wherein it is applied onto hair and skin which has previously been contacted with a cosmetic, personal care or dermatological composition. An example of such a composition is a topcoat composition such as lip gloss or lip balm or a sun protectant composition.

The compositions of the present invention can be provided in a plethora of forms, including but not limited to creams, liquid, gel, cream-gel, lotion, foam, serum, paste, semi-solid, solid stick, stick-gel, or a powder, and may be in the form of a mousse or a spray, and may optionally be packaged as an aerosol, prepared according to the usual methods.

The compositions of the present invention may also be in the form of cleaning products and coatings which can be applied onto non-keratinous substrates such as glass, wood, metal, paper and fabric.

The following examples are intended to illustrate the invention without limiting the scope as a result. The percentages are given on a weight basis.

EXAMPLES

Water Resistance Evaluation

Water resistance of compositions for application onto skin was evaluated according to an in vitro water resistance test for skin ("WR Test I") that is based on a measurement of the quantity one or more organic sunscreens recovered from a substrate initially treated with a composition containing the organic sunscreen(s) after water immersion. The substrate consists of polymethylmethacrylate (PMMA)-coated plates ("PMMA plates") from Europlast, Inc. and were found to be suitable substitute substrates for skin (see Ahn, S., Yang, N., Lee, H. Alternative Evaluation Method In Vitro for the Water Resistant Effect of Sunscreen Products, J. of Skin Research and Technology. Jul. 22, 2007.) The in vitro water resistance test for skin according to the present invention was employed as an alternative to in vivo testing on skin. The test is as follows:

A measured amount (18-20 mg) of a test composition (test sample) containing the organic sunscreen was distributed onto the surfaces of 8 PMMA plates to form treated plates and allowed to dry for 30 to 40 minutes in the dark. Two of the treated plates were designated as the control plates. The rest of the treated plates were designated as the test plates. The test plates were then attached to holders and immersed in a water bath for a specified period of time, such as 30 minutes, wherein the water was stirred at constant speed by a propeller device and the temperature of the water was at 23 degrees centigrade. The plates were then allowed to dry for 30 minutes. The composition remaining on the plates was twice extracted by 35 ml of alcohol (in this case, methanol) from the plate. The combined alcohol extract was diluted to 100 ml with alcohol to form a sample extract solution ("sample extract") from which a 9 ml aliquot was taken and diluted to 25 ml. The absorbance of the final extract solution for each sample was obtained by measuring the ultraviolet (UV) absorbance maximum.

The control plates were not subjected to the water immersion step described above. However, the same alcohol extraction procedure as above was performed on the control plates and the UV absorbance maximum for the control sample extract solution ("control extract") was measured.

The percent water-resistance (% WR) of the test composition is determined as:

% WR(WR Test I)=RA(sample extract)/RA(control extract)×100 wherein RA is the relative absorbance such that:

RA(sample extract)=Absorbance(sample extract)/ Weight of test composition; and

RA(control extract)=Absorbance(control extract)/ Weight of test composition*

*weight of test composition on control plates.

When comparing % WR among several compositions, a higher % WR means that a higher amount of the composition remained on the plate, indicating that the composition is more water resistant.

Example 1

Comparative Water-Resistance Study Following WR Test I

The following skin care creams (test compositions) were formulated:

| | % weight | | | |
|---|---|---|---|---|
| Ingredients | A (base cream) | B | C | D |
| Emulsifier | 2.8 | 2.8 | 2.8 | 2.8 |
| Co-emulsifier | 4.0 | 4.0 | 4.0 | 4.0 |
| Structurant | 3.2 | 3.2 | 3.2 | 3.2 |
| Organic sunscreen(s) | 15 | 15 | 15 | 15 |
| Humectant | 7 | 7 | 7 | 7 |
| Solvent | 7 | 7 | 7 | 7 |
| Preservatives | 1.8 | 1.8 | 1.8 | 1.8 |
| meadowfoam delta-lactone | — | 2 | — | — |
| Aminomethyl propanol (AMP) | — | — | 2 | — |
| meadowfoam delta-lactone/AMP (1:1 molar ratio*) | — | — | — | 2 |
| Water | 57.2 | 57.2 | 57.2 | 57.2 |

*The reaction product was prepared by heating a mixture of a 1:1 molar ratio of meadowfoam delta-lactone and Aminomethyl propanol (AMP) under anhydrous conditions for 1 hour at 100° C.

Creams A, B, C, D were assessed for their water-resistance properties using the procedure described above The results are:

| Compositions | % WR |
|---|---|
| A (Base only) | 83 |
| B (Base + 2% by weight meadowfoam delta-lactone) | 81 |
| C (Base + 2% by weight AMP*) | 83 |
| D (Base + 2% by weight meadowfoam delta-lactone/AMP* reaction product, 1:1 molar ratio) | 91 |

*AMP is aminomethyl propanol (also known as isobutanolamine)

The results from the water resistance test above show that the degree of water resistance by the inventive composition, Cream D, is higher and therefore, significantly better than that of the other creams that did not contain both meadowfoam delta-lactone and AMP since the higher the % WR, the more water-resistant the composition is. This result also demonstrates that the composition containing the reaction product provided water resistance and long lasting and durable hydrophobicity onto a surface, which would extend the beneficial effects provided by the sunscreens or any active ingredient in the cream composition when such a composition is applied onto keratinous substrates such as skin or hair.

Water Resistance Study on Hair

Water resistance of compositions for application onto hair was evaluated according to an in vitro water resistance test for hair ("WR Test II"). Various types of hair, including permed, bleached, relaxed or virgin hair may be used. The WR Test II is based on a measurement of the quantity a water soluble organic sunscreen (designated as a "marker") that is released/ dissolves into water after immersing the hair in water, wherein the hair was initially treated with a composition containing the marker sunscreen. The concentration of organic sunscreen that is released into the water is directly proportional to the degree of water resistance or hydrophobicity imparted to the hair by the composition.

The treatment of the hair samples may performed in one of two ways: (A) directly treated with a test/control composition containing the marker sunscreen ("WR Test IIA"); or (B) first treated with an aqueous solution containing the marker sunscreen, then treated with the test/control composition ("WR Test IIB"). The hair samples may be treated by spraying, massaging, spreading or combing the test/control composition onto the hair or by dipping the hair into said composition. The treated hair samples for both control and test compositions are dried and placed in small perforated baskets. The baskets are then immersed in water and rotated at a constant speed for a period of time (e.g., 180 minutes) at 23 degrees centigrade. The concentrations of benzophenone-4 that is removed or released from the treated hair samples are obtained by measuring the UV absorbance maxima of the water based on a calibration curve.

The percent water-resistance (WR) of the test composition is determined as:

% WR(WR Test IIA or IIB)=100−[RA(Test)/RA(Control)×100] wherein RA is the relative absorbance such that RA(test)=Absorbance(Test)/Weight of treated hair before water immersion; and RA(control)=Absorbance(Control)/Weight of the treated hair before water immersion.

Example 2

Water Resistance Study on Hair following the WR Test IIB

Bleached hair samples were soaked in a 1% by weight of benzophenone-4 in water solution for 30 minutes and allowed to dry overnight at room temperature. Ethanol-based control and test compositions as tabulated below were then applied onto the hair samples for 30 minutes and the resulting treated hair samples were allowed to air dry. Following the WR Test IIB described above, the treated hair samples were immersed in water for 180 minutes and the benzophenone-4 concentration in the water and % WR were measured.

The results are:

| Compositions | Benzophenone-4 concentration (µg/ml) |
|---|---|
| 1: ethanol (control) | 57.7 |
| 2: 1% meadowfoam delta-lactone in ethanol | 55.7 |
| 3: 1% AMP in ethanol | 56.1 |
| 4: 1% aminomethyl propanediol | 58.5 |
| 5: 1% of the meadowfoam delta-lactone/AMP reaction product, 1:1 molar ratio*, in ethanol | 48.0 |
| 6: 1% of the meadowfoam delta-lactone/AMP reaction product, 2:1 molar ratio*, in ethanol | 40.2 |
| 7: 1% of the meadowfoam delta-lactone/ aminomethyl propanediol reaction product, 1:1 molar ratio*, in ethanol | 43.3 |
| 8: 1% of the meadowfoam delta-lactone/ aminomethyl propanediol reaction product, 2:1 molar ratio*, in ethanol | 48.6 |
| 9: 1% of the meadowfoam delta-lactone/ aminomethyl propanediol reaction product, 3:1 molar ratio*, in ethanol | 46.8 |

*Each reaction product was prepared by heating a mixture of a 1:1 molar ratio of meadowfoam delta-lactone and amino alcohol compound under anhydrous conditions for 1 hour at 100° C.

The calculated % WR values for compositions 5, 6, 7, 8 and 9 were 16.77%, 21.66%, 23.82%, 15.3% and 19.80%, respectively.

The results above show that compositions 5 to 9, containing the reaction products, were significantly more water resistant as evidenced by the lower amount of benzophenone-4 that was present in the water compared to amounts of benzophenone-4 corresponding to the other compositions which did not contain the reaction product. This demonstrates that the compositions containing the reaction products provided water resistance properties and long lasting and durable hydrophobicity onto the hair; at the same time, they inhibited the water from passing through the hair and washing the composition off the hair.

It is to be understood that the foregoing describes preferred embodiments of the invention and that modifications may be made therein without departing from the spirit or scope of the invention as set forth in the claims.

What is claimed is:

1. A composition comprising:
   (a) a reaction product of:
      (i) meadowfoam delta-lactone; and
      (ii) at least one amine compound selected from the group consisting of aminomethylpropanol, aminomethyl propanediol, and a mixture thereof; and
   (b) optionally, at least one carrier;
   wherein the composition is water resistant.

2. The composition of claim 1, wherein the molar ratio of (a)(i) to (a)(ii) ranges from about 5:1 to about 1:5, prior to reacting (a)(i) with (a)(ii).

3. The composition of claim 1, wherein (a) is present in an amount of from about 0.05 to about 40% by weight, based on the total weight of the composition.

4. The composition of claim 1, wherein (a) is present in an amount of from about 0.1 to about 30% by weight, based on the total weight of the composition.

5. The composition of claim 1, wherein (b) is chosen from water, oils, alcohols, organic solvents, esters, silicones, waxes, and mixtures thereof.

6. The composition of claim 1, wherein (b) is a non-reactive solvent.

7. The composition of claim 1, wherein the composition does not require the presence of a monoacid in order to be water resistant.

8. The composition of claim 1, wherein the composition further comprises at least one benefit agent chosen from sunscreen agents, cosmetically active agents, dermatologically active agents, humectants, moisturizing agents, colorants, hair straightening/relaxing agents, film forming agents, shine agents, conditioning agents, reducing agents, emollients, vitamins, antidandruff agents, plant extracts, antiperspirants, and pharmaceutical agents.

9. The composition of claim 1, wherein the composition is anhydrous.

10. A composition comprising:
   (a) from about 0.5 to about 10% by weight, based on the total weight of the composition, of a reaction product of:
      (i) meadowfoam delta-lactone; and
      (ii) at least one amino alcohol compound chosen from aminomethylpropanol, aminomethyl propanediol, and mixtures thereof;
   (b) at least one carrier; and
   (c) optionally, at least one benefit agent;
   wherein the molar ratio of (a)(i) to (a)(ii) ranges from about 2:1 to about 1:2, prior to reacting (a)(i) with (a)(ii); and wherein the composition is water resistant.

11. The composition of claim 1, wherein the reaction product is obtained by reacting the amine compound with a carbonyl group of the meadowfoam delta-lactone, which opens the heterocyclic ring and forms the reaction product.

12. The composition of claim 10, wherein the reaction product is obtained by reacting the amine compound with a carbonyl group of the meadowfoam delta-lactone, which opens the heterocyclic ring and forms the reaction product.

* * * * *